United States Patent [19]

Broger et al.

[11] Patent Number: 5,481,008

[45] Date of Patent: Jan. 2, 1996

[54] PROCESS FOR THE PREPARATION OF OPTICALLY ACTIVE COMPOUNDS

[75] Inventors: Emil A. Broger, Magden; Martin Karpf, Reinach; Ulrich Zutter, Basel, all of Switzerland

[73] Assignee: Hoffmann-La Roche Inc., Nutley, N.J.

[21] Appl. No.: 298,734

[22] Filed: Aug. 31, 1994

[30] Foreign Application Priority Data

Sep. 13, 1993 [CH] Switzerland .................... 2738/93

[51] Int. Cl.⁶ .................... C07D 309/32; C07D 309/30
[52] U.S. Cl. .................... 549/292; 549/293; 549/294
[58] Field of Search .................... 549/292, 293, 549/294

[56] References Cited

U.S. PATENT DOCUMENTS

| | | | |
|---|---|---|---|
| 4,556,740 | 12/1985 | Hansen et al. | 568/13 |
| 5,245,056 | 9/1993 | Karpf et al. | 549/510 |

FOREIGN PATENT DOCUMENTS

| | | |
|---|---|---|
| 9228413 | 11/1991 | Australia . |
| 104375 | 8/1983 | European Pat. Off. . |
| 398132 | 5/1990 | European Pat. Off. . |
| 443449 | 2/1991 | European Pat. Off. . |
| 524495 | 7/1992 | European Pat. Off. . |
| 543245 | 11/1992 | European Pat. Off. . |

OTHER PUBLICATIONS

Abstract (corresponding to EP 398132) (1990).

*Primary Examiner*—C. Warren Ivy
*Assistant Examiner*—Ba K. Trinh
*Attorney, Agent, or Firm*—George M. Gould; George W. Johnston; Ellen Ciambrone Coletti

[57] ABSTRACT

A catalytic process for the manufacture of optically active compounds of the formula

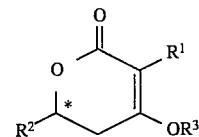

wherein
$R^1$ and $R^2$ are alkyl, which is optionally interrupted by an O atom in a position other than the α- or β-position, or optionally substituted benzyl,
$R^3$ is hydrogen, lower alkyl, optionally substituted benzyl, —CO—$R^4$, —COO$R^4$ or —CON$R_2^4$, and
$R^4$ is lower alkyl or aryl,
comprising asymmetrically hydrogenating a compound of the formula

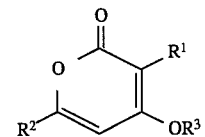

wherein $R^1$, $R^2$ and $R^3$ have the above significance, in the presence of a complex of an optically active, preferably atropisomeric, diphospine ligand with a metal of Group VIII.

7 Claims, No Drawings

PROCESS FOR THE PREPARATION OF OPTICALLY ACTIVE COMPOUNDS

BRIEF SUMMARY OF THE INVENTION

The present invention relates to a catalytic process for the manufacture of optically active compounds of the formula

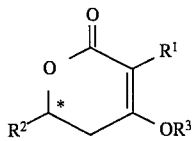

I wherein
- $R^1$ and $R^2$ are alkyl, which is optionally interrupted by an O atom in a position other than the α- of β-position, or optionally substituted benzyl,
- $R^3$ is hydrogen, lower alkyl, optionally substituted benzyl, —CO—$R^4$, —COO$R^4$ or —CON$R_2^4$, and
- $R^4$ is lower alkyl or aryl comprising asymmetrically hydrogenating a compound of the formula

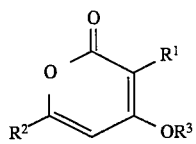

II wherein $R^1$, $R^2$, R3 have the above significance, in the presence of a complex of an optically active, preferably atropisomeric, diphosphine ligand with a metal of Group VIII.

DETAILED DESCRIPTION OF THE INVENTION

The present invention relates to a catalytic process for the manufacture of optically active compounds of the formula

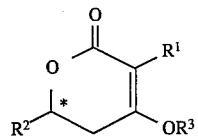

I wherein
- $R^1$ and $R^2$ are alkyl, which is optionally interrupted by an O atom in a position other than the α- or β-position, or optionally substituted benzyl,
- $R^3$ is hydrogen, lower alkyl, optionally substituted benzyl, —CO—$R^4$, —COO$R^4$ or —CON$R_2^4$, and
- $R^4$ is lower alkyl or aryl.

The compounds of formula I are known compounds and are valuable intermediates for pharmaceutically usable end products. For example, they can be converted into pharmaceuticals for the inhibition of pancreas lipase as described in EP 443 449, corresponding to U.S. Pat. No. 5,245,056, which is hereby incorporated by reference.

The object of the present invention is to find a direct access to optically active compounds of formula I, as a result of which a subsequent racemate resolution is unnecessary.

The process in accordance with the invention comprises asymmetrically hydrogenating a compound of the formula

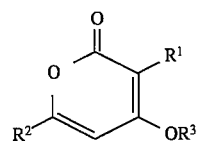

II wherein $R^1$, $R^2$, $R^3$ have the above significance, in the presence of a complex of an optically active, preferably atropisomeric, diphosphine ligand with a metal of Group VIII.

As optically active metal-diphosphine complexes for the process in accordance with the invention there especially come into consideration optically active ruthenium complexes of the formulas

| | |
|---|---|
| 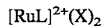 $[RuL]^{2+}(X)_2$ | III-a |
| 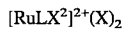 $[RuLX^2]^{2+}(X)_2$ | III-b |
| 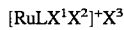 $[RuLX^1X^2]^+X^3$ | III-c |
|  $RuL(X^4)_2$ | III-d | wherein
- X is $BF_4^-$, $ClO_4^-$, $B(phenyl)_4^-$, $SbF_6^-$, $PF_6^-$ or $Z^1$—$SO_3^-$,
- $X^1$ is halide,
- $X^2$ is benzene, hexamethylbenzene or p-cymene,
- $X^3$ is halide, $ClO_4^-$, $B(phenyl)_4^-$, $SbF_6^-$, $PF_6^-$, $Z^1$—$SO_3^-$ or $BF_4^-$,
- $X^4$ is an anion $Z^2$—$COO^-$ or an anion $Z^3$—$SO_3^-$,
- $Z^1$ is halogenated lower alkyl or halogenated phenyl,
- $Z^2$ is lower alkyl, phenyl, halogenated lower alkyl or halogenated phenyl,
- $Z^3$ is lower alkyl or phenyl and
- L is an optically active, atropisomeric diphosphine ligand of the formula

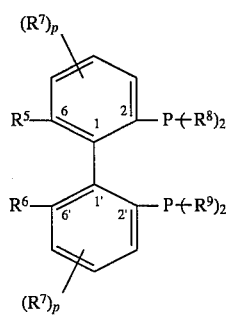

IV or of the formula

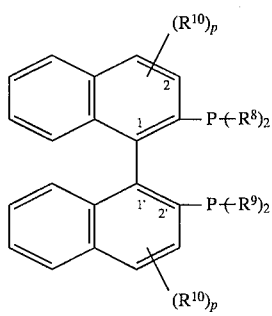

in the (S) or (R) form, wherein $R^5$ and $R^6$ each independently are lower alkyl, lower alkoxy, di-(lower alkyl)-amino, hydroxy, protected hydroxy, hydroxymethyl or protected hydroxymethyl, or $R^5$ and $R^6$ together signify a divalent group

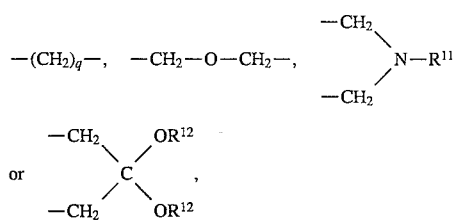

$R^7$ is hydrogen, lower alkyl or lower alkoxy, $R^8$ and $R^9$ each independently represent cyclo-alkyl, unsubstituted or substituted phenyl or a 5-membered heteroaromatic ring, with the proviso that at least one of the residues $R^8$ and $R^9$ represents a substituted phenyl ring or a 5-membered heteroaromatic ring, $R^{10}$ is halogen, hydroxy, lower alkyl, amino, acetamido, nitro or sulpho, preferably in the 5,5'-position, $R^{11}$ is lower alkyl, phenyl or benzyl, $R^{12}$ is lower alkyl or both $R^{12}$'s together represent a di- or trimethylene group, p is zero or the number 1, 2 or 3 and q is the number 3, 4 or 5.

In connection with the compounds of formulas I to V, the following definitions of the terms apply irrespective of whether the terms appear alone or in combination.

The term "alkyl, which is optionally interrupted by an O atom in a position other than the α-or β-position," signifies, in the scope of the present Application, alkyl groups with 1 to 17 carbon atoms, such as, for example, methyl, ethyl, propyl, isopropyl, butyl, isobutyl, pentyl, hexyl, heptyl, octyl, nonyl, decyl, undecyl, dodecyl, tridecyl, tetradecyl, pentadecyl, hexadecyl, heptadecyl, ethoxypropyl, ethoxybutyl, propyloxyethyl and the like.

The term "optionally substituted benzyl" embraces benzyl or benzyl which is substituted in the 2-, 3-, 4-, 5- and/or 6-position with lower alkyl or lower alkoxy, such as, for example, 4-methylbenzyl, 4-methoxybenzyl, 3-methylbenzyl and the like.

Lower alkyl signifies, in the scope of the present invention, straight-chain or branched alkyl groups with 1 to 5 carbon atoms, such as, for example, methyl, ethyl, propyl, isopropyl, butyl, isobutyl, tert.-butyl, pentyl, isopentyl or tert.-pentyl. The term "lower alkoxy" signifies groups in which the alkyl residue has the foregoing significance.

Aryl signifies, in the scope of the present Application, a phenyl residue which can be not only unsubstituted, but also mono- or multiply-substituted in the ortho-, meta- or para-position. Substituents which especially come into consideration are lower alkyl or lower alkoxy groups or halogen, especially chlorine. Phenyl and tolyl are especially preferred aryl groups.

Halogen or halide means fluorine, chlorine, bromine or iodine, but especially chlorine, bromine or iodine.

The term "halogenated lower alkyl" signifies, in the scope of the present Application, alkyl groups with 1 to 4 carbon atoms and with a variable number of halogen atoms, especially chlorine or fluorine. Especially preferred halogenated lower alkyl groups are, for example, perfluorinated and perchlorinated lower alkyl groups, such as, for example, trifluoromethyl, pentafluoroethyl and the like.

The term "halogenated phenyl" preferably signifies perfluorophenyl or perfluorophenyl.

The term "di-(lower alkyl)-amino" signifies, in the scope of the present invention, for example, dimethylamino, diethylamino and the like.

As protecting groups for the hydroxy groups there come into consideration, in the scope of the present invention, especially the usual ether-forming groups, such as, for example, benzyl, allyl, benzyloxymethyl, lower alkoxymethyl or also 2-methoxyethoxymethyl.

Cyclo-alkyl embraces, in the scope of the present invention, cyclic alkyl groups with 5 to 8 carbon atoms, but especially cyclo-pentyl or cyclo-hexyl.

Substituted phenyl denotes, in connection with compounds of formulas IV and V, phenyl which is substituted, preferably in the 3-and 5-position, with electron-donating groups, such as, for example, groups of the formulas

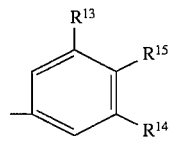 VI-a

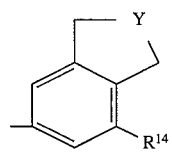 VI-b or

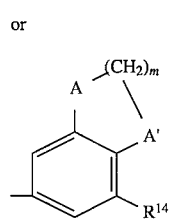 VI-c wherein

Y is $(-CH_2-)_m$, oxygen, sulphur or $-N-R^{17}$,

A and A' each independently are $-CH_2-$, $-CR^{13}R^{14}-$, oxygen, sulphur or $-N-R^{17}$, $R^{13}$ and $R^{14}$ each independently are lower alkyl (such as methyl, ethyl, isopropyl, isobutyl, tert.-butyl, isopentyl or tert.-pentyl), lower alkoxy (such as methoxy, ethoxy), trialkylsilyl (such as trimethylsilyl, triethylsilyl), cyclo-alkyl (such as cyclo-pentyl, cyclo-hexyl) or benzyl or one of the residues $R^{13}$ or $R^{14}$ also signifies hydrogen, $R^{15}$ is hydrogen, lower alkyl, lower alkoxy, trialkylsilyl (such as, for example, trimethylsilyl or triethylsilyl), di-(lower alkyl)-amino or lower thioalkyl, $R^{17}$ is lower alkyl, especially methyl, and m is a whole number 1, 2 or 3.

The term "5-membered heteroaromatic ring", in the scope of the present Application, stands for a substituent of the formula

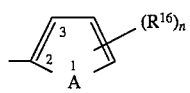 VI-d

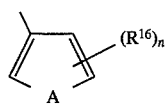 VI-e

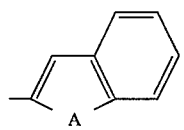 VI-f or

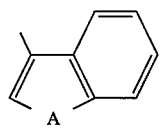 VI-g

Moreover, in formulas VI-d to VI-g

A is oxygen, sulphur or $-N-R^{17}$, $R^{16}$ is hydrogen, lower alkyl, especially methyl, or lower alkoxy, especially methoxy, $R^{17}$ is lower alkyl, especially methyl, and n is zero, 1 or 2.

The asymmetric hydrogenation in accordance with the invention of compounds of formula II to compounds of formula I can be effected in a suitable organic solvent which is inert under the reaction conditions. As such solvents there especially come into consideration lower alcohols, such as, for example, methanol, ethanol, isopropanol; or mixtures of such alcohols with halogenated hydrocarbons, such as, for example, methylene chloride, chloroform, hexafluorobenzene and the like; or mixtures with ethers, such as, for example, diethyl ether, tetrahydrofuran or dioxan; mixtures of the aforementioned alcohols with esters, such as, for example, ethyl acetate, or with carboxylic acids, such as, for example, formic acid, acetic acid and the like, or also with ketones, such as, for example, acetone, methyl ethyl ketone or diethyl ketone, or with water can be used.

Preferably, the reaction is carried out in methanol, ethanol or isopropanol or in mixtures of such alcohols with the aforementioned halogenated hydrocarbons, with the aforementioned ethers, with ketones or also with water. However, the aforementioned alcohols or mixtures, such as, for example, methanol/water or methanol/diethyl ether/tetrahydrofuran and the like, are especially suitable for the process in accordance with the invention.

The hydrogenation is conveniently carried out at temperatures between about 0° C. and about 100° C., preferably in the temperature range of about 20° C. to about 80° C., and at a pressure of about 1 to about 100 bar, preferably of about 5 to about 70 bar.

The molar ratio between the compounds of formula II to be hydrogenated and the ruthenium in the complexes of formula III-a to III-d conveniently lies between about 20,000 and about 20, preferably between about 10,000 and about 100.

The ligands of formulas IV and V are known compounds or analogs of known compounds which can be prepared readily in a manner analogous to the preparation of known ligands.

The compounds of formulas IV and V in which $R^8$ and $R^9$ are the same can be prepared, for example, as described in EP 104 375 corresponding to U.S. Pat. No. 4,556,740, or also in EP 398 132. The preparation of compounds in which $R^8$ and $R^9$ are different from one another is effected analogously thereto, but in two steps, as described, for example, in EP 543 245.

The complexes of formulas III-b and III-c can be prepared in a known manner. Complexes of formula III-d can be prepared, for example, by reacting compounds of formula IV or V with compounds, which can yield ruthenium, in a suitable inert organic or aqueous solvent. The complexes of formula III-a can be prepared from the compounds III-d by reaction with HX in which X has the aforementioned significance, but signifies especially $BF_4-$ or $CF_3SO_3-$.

The enantioselective hydrogenation of compounds of formula II is preferably carried out in the presence of ruthenium-diphosphine complexes of formula III-a, especially in the presence of ruthenium-diphosphine complexes of formula III-a and an excess of HX or another suitable acid, such as, for example, a perfluorinated carboxylic acid.

Of the ligands of formulas IV and V which, inter alia, are usable in the scope of the present invention there are preferred those of formula IV. Especially preferred ligands of formula IV are those in which $R^5$ and $R^6$ are the same and signify methyl or methoxy, p is equal to zero and $R^8$ and $R^9$ have the same significance and represent substituted phenyl, preferably a group of formula VI-a. Groups of formula VI-a in which $R^{13}$ and $R^{14}$ are the same and signify methyl, isopropyl, tert.-butyl, tert.-pentyl, methoxy, trimethylsilyl or triethylsilyl and $R^{15}$ signifies hydrogen, methoxy or dimethylamino are especially preferred.

Examples of especially preferred ligands of formula IV are (6,6'-dimethoxybiphenyl-2,2'-diyl)bis[bis(3,4,5-trimethoxyphenyl)phosphine](3,4,5-MeO-MeOBIPHEP)

(6,6'-dimethoxybiphenyl-2,2'-diyl)bis[bis(3,5-dimethyl-4-dimethylaminophenyl)phosphine](DMAXyl-MeOBIPHEP)

(6,6'-dimethoxybiphenyl-2,2'-diyl)bis[bis(3,5-bis(trimethylsilyl)phenyl)phosphine](3,5-TMS-MeOBIPHEP)

(6,6'-dimethoxybiphenyl-2,2'-diyl)bis[bis(3,5-bis(triethylsilyl)phenyl)phosphine](3,5-TES-MeOBIPHEP)

(6,6'-dimethoxybiphenyl-2,2'-diyl)bis[bis(3,5-diisopropylphenyl)phosphine](3,5-iPr-MeOBIPHEP)

(6,6'-dimethoxybiphenyl-2,2'-diyl)bis[bis(3,5-ditert.-butylphenyl)phosphine](3,5-tBu-MeOBIPHEP)

(6,6'-dimethoxybiphenyl-2,2'-diyl)bis[bis(3,5 -ditert.-pentylphenyl)phosphine](3,5-tPen-MeOBIPHEP)

(6,6'-dimethoxybiphenyl-2,2'-diyl)bis[bis(3,5-dimethylphenyl)phosphine](Xyl-MeOBIPHEP)

(6,6'-dimethoxybiphenyl-2,2'-diyl)bis[bis(3,5-diisopropyl-4-methoxyphenyl)phosphine](3,5-iPr-4-MeO-MeOBIPHEP)

(6,6'-dimethoxybiphenyl-2,2'-diyl)bis[bis(3,5-ditert.-butyl-4-methoxyphenyl)phosphine](3,5-tBu-4-MeO-MeOBIPHEP)

(6,6'-dimethoxybiphenyl-2,2'-diyl)bis[bis(3,5-ditert.-pentyl-4-methoxyphenyl)phosphine](3,5-tPen-4-MeO-MeOBIPHEP)

The following Examples illustrate the invention and are not in any way a limitation thereof. In these Examples the abbreviations used have the following significance:

OAc acetoxy

HPLC high pressure liquid chromatography

RT room temperature

HV high vacuum: ~0.1 mbar

GC capillary gas chromatography. The product samples were acetylated with acetic anhydride/pyridine or silylated with N,O-bis(trimethylsilyl)acetamide/5% trichlorosilane in pyridine. Catalyst-containing samples were dissolved in methylene chloride and the solution was filtered through a small amount of silica gel in order to separate the catalyst.

o.p. optical purity of (R)-3-hexyl-5,6-dihydro-4-hydroxy-6-undecyl-2H-pyran-2-one, $[\alpha]_D^{20} = -45.6°$ (c=1, dioxan).

ee enantiomeric excess of 3-hexyl-5,6-dihydro-4-methoxy-6-undecyl-2H-pyran-2-one. The methyl ether originated from the hydrogenation or was prepared by methylating the corresponding dihydropyrone using methyl orthoformate/methanol and p-toluenesulphonic acid as the catalyst. The ee determination was effected by high pressure liquid chromatography (HPLC) on a Chiralcel-OD phase.

DHP 3-hexyl-5,6-dihydro-4-hydroxy-6-undecyl-2H-pyran-2-one (dihydropyrone)

DHPM 3-hexyl-5,6-dihydro-4-methoxy-6-undecyl-2H-pyran-2-one (dihydropyrone methyl ether).

All temperatures are given in degrees Celsius.

EXAMPLE 1 a) 19.6 mg (0.06 mmol) of di($\eta^2$-acetato)-($\eta^4$-cycloocta-1,5-diene)ruthenium(II) and 61.9 mg (0.060 mmol) of (S)-3,5-tBu-MeOBIPHEP were dissolved in 7.5 ml of diethyl ether and 2.5 ml of tetrahydrofuran in a Schlenk tube in a glove box (argon, <1 ppm oxygen) and the solution was stirred at 40° overnight. After cooling, 2.5 ml (0.015 mmol) of catalyst solution were added to 6.5 ml of diethyl ether/tetrahydrofuran (3:1, v/v) and the resulting solution was treated with a solution of 26.3 mg (0.15 mmol) of 50 percent aqueous $HBF_4$ in 7.5 ml of methanol. The yellow catalyst solution was stirred at room temperature for 1.5 h.

b) The glass attachment of a 30 ml autoclave was charged in a glove box with 1.05 g (3.00 mmol) of 3-hexyl-4-hydroxy-6-undecyl-2H-pyran-2-one, 13.5 ml of methanol and with the catalyst solution (S/C 200) prepared according to a). The hydrogenation was carried out at 60° and 60 bar for 48 h while stirring with a magnetic rod.

The yellow hydrogenation solution was evaporated at 35°/20 mbar on a rotary evaporator. The residue (1.02 g of yellow crystals) consisted, according to GC analysis, of 59% of 3-hexyl-5,6-dihydro-4-hydroxy-6-undecyl-2H-pyran-2.-one, 10% 3-hexyl-5,6-dihydro-4-methoxy-6-undecyl-2H-pyran-2-one 5% of a mixture of the 4 diastereomeric saturated lactones and 22% of educt. In order to determine the enantioselectivity, 0.71 g of the residue was chromatographed on 40 g of silica gel. Methylene chloride eluted 320 mg of (R)-dihydropyrone, $[\alpha]_D^{20} = -38.4°$, and, after mixed fractions, 27 mg of pure (R)-dihydropyrone methyl ether, 91.9% ee.

EXAMPLE 2 a) A solution of 15.0 mg (0.012 mmol) of $Ru(OAc)_2$[(S)-3,5-tBu-MeOBIPHEP]in 12.5 ml of methanol was treated in a glove box with a solution of 21.1 mg (0.12 mmol) of 50 percent aqueous $HBF_4$ in 25 ml of methanol. The catalyst solution was stirred at room temperature for 1.5 h.

b) A 185 ml autoclave was charged in a glove box with 4.21 g (12.0 mmol) of 3-hexyl-4-hydroxy-6-undecyl-2H-pyran-2-one, 15 ml of methanol and with the catalyst solution (S/C 1,000) prepared according to a). The hydrogenation was carried out at 60° and 60 bar and while stirring vigorously for 48 h. After cooling, the yellow crystal slurry was evaporated at 40°/18 mbar on a rotary evaporator. The residue (4.3 g of yellow crystallizate), which, according to GC analysis, consisted of 73% of 3-hexyl-5,6-dihydro-4-hydroxy-6-undecyl-2H-pyran-2-one, 20% of 3-hexyl-5,6-dihydro-4-methoxy-6-undecyl-2H-pyran-2-one and 5% of a mixture of the 4 diastereomeric saturated lactones, was chromatographed on 150 g of silica gel. Methylene chloride eluted 210 mg of (R)-dihydropyrone, $[\alpha]_D^{20} = -42.0°$ (92% o.p.), 3.44 g of mixed fractions consisting of dihydropyrone and dihydropyrone methyl ether and 120 mg of (R)-dihydropyrone methyl ether, 92.1% ee.

TABLE 1

Asymmetric hydrogenations of 3-hexyl-4-hydroxy-6-undecyl-2H-pyran-2-one in the presence of [RuL]($BF_4$)$_2$ as the catalyst in methanol-diethyl ether-tetrahydrofuran (7:2.25:0.75, v/v) and at 60 bar[1]

| Ex. No. | L | Ru/$HBF_4$ mol/mol | S/C mol/mol | T °C. | c % | Conversion % | (h) | Selectivity[2] (DHP + DHPM) % | o.p.[3] % | ee[4] % | Config. |
|---|---|---|---|---|---|---|---|---|---|---|---|
| 3 | (S)-3,5-TMS-MeOBIPHEP | 2 | 25 | 40 | 4 | 37 | (44) | 94 | 91.0 | | R |
| 4 | (S)-DMAXyl-MeOBIPHEP | 2 | 25 | 60 | 4 | 98 | (46) | 95 | 89.5 | 89.5 | R |
| 5 | (S)-3,4,5-MeO-MeOBIPHEP | 10 | 100 | 60 | 4 | 46 | (48) | 78 | | 90.0 | R |
| 6 | (R)-3,5-TES-MeOBIPHEP | 10 | 100 | 60 | 4 | 63 | (51) | 73 | 86.4 | | S |
| 7 | (S)-3,5-tBu-MeOBIPHEP | 10 | 100 | 60 | 4 | 99 | (24) | 74 | | 93.5 | R |
| 8 | (R)-3,5-tBu-MeOBIPHEP | 10 | 1000 | 80 | 15 | 41 | (48) | 90 | | 87.6 | R |
| 9 | (R)-3,5-tBu-4-MeO-MeOBIPHEP | 10 | 1000 | 60 | 15 | 74 | (46) | 95 | | 94.0 | R |
| 10 | (R)-3,5-iPr-4-MeO-MEOBIPHEP | 10 | 1000 | 60 | 15 | 54 | (20) | 98 | — | 93.2 | R |

[1]Catalyst preparation Ex. 3–7 and 9 and 10 analogously to Example 1, Ex. 8 analogously to Example 2
[2](DHP + DHPM)/conversion × 100
[3]Optical purity of chromatographically purified DHP
[4]ee of DHPM

TABLE 2

Asymmetric hydrogenations of 3-hexyl-4-hydroxy-6-undecyl-2H-pyran-2-one (c = 15) at 60 bar[a]

| Ex. No. | L | HX | Ru/X | S/C | Solv. v/v | Conversion % | h | Selectivity DHP | DHP-ether | ee % | Config. |
|---|---|---|---|---|---|---|---|---|---|---|---|
| 11 | (S)-3,5-tBu-MeOBIPHEP | $BF_4^-$ | 10 | 1000 | MeOH/Et$_2$O 7:3 | 98 | 43 | 80 | 12 | 93.0 | R |
| 12 | (S)-3,5-tBu-MeOBIPHEP | $BF_4^-$ | 10 | 1000 | MeOH/H$_2$O 99:1 | 100 | 48 | 88 | 5 | 93.5 | R |
| 13 | (R)-3,5-tBu-MeOBIPHEP | $BF_4^-$ | 10 | 1000 | MeOH/H$_2$O 97:3 | 99 | 44 | 92 | 1 | 89.6 | S |
| 14 | (R)-3,5-tBu-MeOBIPHEP | $BF_4^-$ | 10 | 1000 | EtOH | 50 | 48 | 80 | 6[b] | 95.8 | S |
| 15 | (R)-3,5-tBu-MeOBIPHEP | $BF_4^-$ | 10 | 1000 | Isopropanol | 100 | 48 | 97 | <1[c] | 95.8 | S |
| 16 | (R)-3,5-tBu-MeOBIPHEP | $BF_4^-$ | 10 | 2000 | MeOH | 94 | 48 | 93 | 2 | 91.3 | S |
| 17 | (S)-3,5-tBu-MeOBIPHEP | $BF_4^-$ | 20 | 2000 | MeOH | 58 | 20 | 86 | 4 | 92.4 | R |
| 18 | (S)-3,5-tBu-4-MeO-MeOBIPHEP | $BF_4^-$ | 20 | 2000 | MeOH | 42 | 20 | 87 | 1 | 93.6 | R |
| 19 | (S)-3,5-tBu-4-MeO-MeOBIPHEP | $CF_3SO_3^-$ | 20 | 2000 | MeOH | 29 | 20 | 65 | 20 | 94.2 | R |
| 20 | (S)-3,5-TMS-MeOBIPHEP | $BF_4^-$ | 10 | 1000 | MeOH | 54 | 20 | 87 | 5 | 91.3 | R |
| 21 | (S)-3,5-tBu-4-MeO-MeOBIPHEP | $BF_4^-$ | 20 | 2000 | MeOH/C$_6$F$_6$ 7:3 | 30 | 20 | 89 | 5 | 94.5 | R |

[a] Catalyst preparation analogously to Example 2
[b] DHP-ethyl ether
[c] DHP-isopropyl ether
MeOH = methanol
Et$_2$O = diethylether
EtOH = ethanol

EXAMPLE 22 a) 13.1 mg (0.040 mmol) of di($\eta^2$-acetato)-($\eta^4$-cycloocta-1,5-diene)ruthenium(II) and 41.3 mg (0.040 mmol) (S)-3,5-tBu-MeOBIPHEP were dissolved in 2.25 ml of diethyl ether and 0.75 ml of tetrahydrofuran in a Schlenk tube in a glove box (argon, <1 ppm oxygen) and the solution was stirred at 40° overnight. After cooling, a solution of 14 mg (0.08 mmol) of 50 percent aqueous HBF$_4$ in 2.5 ml of methanol was added. The yellow catalyst solution was stirred at room temperature for 1.5 h.

b) The glass attachment of a 30 ml autoclave was charged in a glove box with 0.36 g (1.00 mmol) of 3-hexyl-4-methoxy-6-undecyl-2H-pyran-2-one, 4.5 ml of methanol and with the catalyst solution prepared according to a). The hydrogenation was carried out at 60° and 60 bar for 40 hours while stirring with a magnetic rod.

The yellow hydrogenation solution was evaporated at 35°/20 mbar on a rotary evaporator. The residue (0.35 g of yellow crystals) consisted of 71% of 3-hexyl-5,6-dihydro-4-methoxy-6-undecyl-2H-pyran-2-one and 21% of educt according to GC analysis. In order to determine the enantioselectivity, a solution of the residue in methylene chloride was filtered through a small amount of silica gel and the eluate, after evaporation, was analyzed by HPLC: 53% ee.

EXAMPLE 23 a) A solution of 16.4 mg (0.012 mmol) of Ru(OAc)$_2$[(S)-3,5-tBu-4-MeO-MeOBIPHEP] in 12.5 ml of methanol was treated in a glove box with a solution of 13.7 mg (0.12 mmol) of trifluoroacetic acid in 2.5 ml of methanol and the catalyst solution was stirred at room temperature for 1.5 h.

b) A 185 ml autoclave was charged in a glove box with 4.21 g (12.0 mmol) of 3-hexyl-4-hydroxy-6-undecyl-2H-pyran-2-one, 15 ml of methanol and with the catalyst solution (S/C 1,000) prepared according to a). The hydrogenation was carried out at 60° and 60 bar and for 24 h. while stirring vigorously. After cooling, the yellow crystal slurry was evaporated at 40°/18 mbar on a rotary evaporator. The residue (4.2 g of yellow crystallizate) consisted of 46% of educt, 48% of 3-hexyl-5,6-dihydro-4-hydroxy-6-undecyl-2H-pyran-2-one and 1% of a mixture of the 4 diastereomeric saturated lactones according to GC analysis.

For the ee determination, the mixture was treated with methyl orthoformate/methanol and a catalytic amount of p-toluenesulphonic acid and analyzed by HPLC: 87.8% ee (R).

EXAMPLE 24 a) A solution of 16.4 mg (0.012 mmol) of Ru(OAc)$_2$[(S)-3,5-tBu-4-MeO-MeOBIPHEP] in 12.5 ml of methanol was treated in a glove box with a solution of 4.2 mg (0.024 mmol) of 50 percent aqueous HBF$_4$ in 2.5 ml of methanol and the solution was stirred at room temperature for 1.5 h. Then, 44.6 mg (0.096 mmol) of perfluoropelargonic acid were added and the catalyst solution was stirred for 15 min.

b) A 185 ml autoclave was charged in a glove box with 4.21 g (12.0 mmol) of 3-hexyl-4-hydroxy-6-undecyl-2H-pyran-2-one, 15 ml of methanol and with the catalyst solution (S/C 1,000) prepared according to a). The hydrogenation was carded out at 60°and 60 bar and for 20 hours while stirring vigorously. After cooling, the yellow crystal slurry was evaporated at 40°/18 mbar on a rotary evaporator. The residue (4.2 g of yellow crystallizate) consisted of 51% of educt, 44% of 3-hexyl-5,6-dihydro-4-hydroxy-6-undecyl-2H-pyran-2-one, 2% of 3-hexyl-5,6-dihydro-4-methoxy-6-undecyl-2H-pyran-2-one and 1% of a mixture of the 4 diastereomeric saturated lactones according to GC analysis.

For the ee determination, the mixture was treated with methyl orthoformate/methanol and a catalytic amount of p-toluenesulphonic acid and analyzed by HPLC: 92.8% ee (R).

We claim:

1. A process for the enantioselective manufacture of an optically active compound of the formula

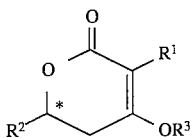   I wherein $R^1$ and $R^2$ are alkyl, which is optionally interrupted by an O atom in a position other than the α- or β-position, or optionally substituted benzyl, $R^3$ is hydrogen, lower alkyl, optionally substituted benzyl, —CO—$R^4$, —COO$R^4$ or —CON$R_2^4$, and $R^4$ is lower alkyl or aryl, which process comprises asymmetrically hydrogenating a compound of the formula

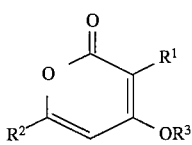   II wherein $R^1$, $R^2$ and $R^3$ have the significances given above, in the presence of a complex of an optically active, atropisomeric diphosphine ligand with a metal of Group VIII.

2. The process according to claim 1, wherein the complex is selected from

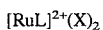   III-a

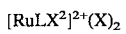   III-b

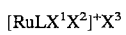   III-c or

   III-d wherein

X is $BF_4^-$, $ClO_4^-$, B(phenyl)$_4^-$, $SbF_6^-$, $PF_6^-$ or $Z^1$—$SO_3^-$, $X^1$ is halide, $X^2$ is benzene, hexamethylbenzene or p-cymene, $X^3$ is halide, $ClO_4^-$, B(phenyl)$_4^-$, $SbF_6^-$, $PF_6^-$, $Z^1$—$SO_3^-$ or $BF_4^-$, $X^4$ is an anion $Z^2$—COO$^-$ or an anion $Z^3$—$SO_3^-$, $Z^1$ is halogenated lower alkyl or halogenated phenyl, $Z^2$ is lower alkyl, phenyl, halogenated lower alkyl or halogenated phenyl, $Z^3$ is lower alkyl or phenyl and L is an optically active, atropisomeric diphosphine ligand of the formula

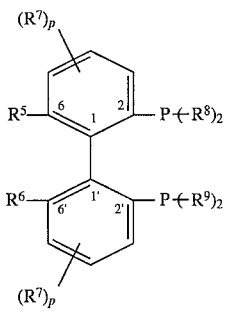   IV or of the formula

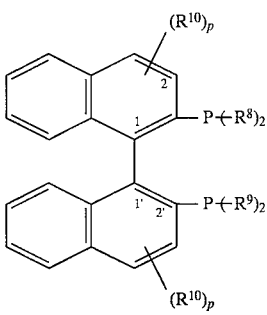   V in the (S) or (R) form, wherein $R^5$ and $R^6$ each independently are lower alkyl, lower alkoxy, di-(lower alkyl)-amino, hydroxy, protected hydroxy, hydroxymethyl or protected hydroxymethyl, or $R^5$ and $R^6$ together signify a divalent group

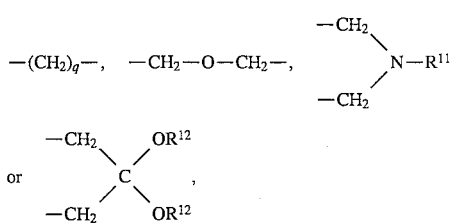

$R^7$ is hydrogen, lower alkyl or lower alkoxy, $R^8$ and $R^9$ each independently are cyclo-alkyl, unsubstituted or substituted phenyl or a 5-membered heteroaromatic, with the proviso that at least one of the residues $R^8$ and $R^9$ is a substituted phenyl ring or a 5-membered heteroaromatic ring, $R^{10}$ is halogen, hydroxy, lower alkyl, amino, acetamido, nitro or sulpho, $R^{11}$ is lower alkyl, phenyl or benzyl, $R^{12}$ is lower alkyl or both $R^{12}$'s together are a di- or trimethylene group, p is zero or the number 1, 2 or 3 and q is the number 3, 4 or 5.

3. The process according to claim 2, wherein the complex is

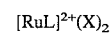   III-a wherein X is $BF_4^-$ or $CF_3SO_3^-$ and L is

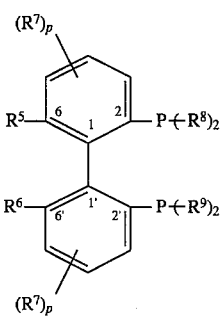 IV in the (R) or in the (S) form, wherein

R$^5$ and R$^6$ are the same and are methyl or methoxy, p is zero, and

R$^8$ and R$^9$ are the same and represent a substituted phenyl.

4. The process according to claim 3, wherein R$^8$ and R$^9$ have the same significance and represent

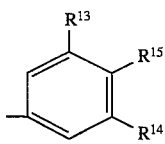 VI-a wherein

R$^{13}$ and R$^{14}$ each independently are lower alkyl, lower alkoxy, trialkylsilyl, cyclo-alkyl or benzyl or one of the residues R$^{13}$ or R$^{14}$ also signifies hydrogen, and R$^{15}$ is hydrogen, hydroxy, lower alkyl, lower alkoxy, trialkylsilyl or di-(lower alkyl)-amino.

5. The process according to claim 4, wherein R$^{13}$ and R$^{14}$ are S the same and signify methyl, methoxy, isopropyl, tert.-butyl, tert.-pentyl or trimethylsilyl; and R$^{15}$ is hydrogen or methoxy.

6. The process according to claim 1, wherein the asymmetric hydrogenation of a compound of formula II is carried out in a lower alcohol or in a mixture of a lower alcohol with ether or water at a temperature between 0° to 100° C.

7. The process according to claim 6, wherein R$^1$ is a straight-chain alkyl group with 5–17 carbon atoms, R$^2$ is a straight-chain alkyl group with 1 to 7 carbon atoms R$^3$ is hydrogen and the complex is [RuL]$^{2+}$(X)$_2$ III a.

* * * * *

UNITED STATES PATENT AND TRADEMARK OFFICE
CERTIFICATE OF CORRECTION

PATENT NO.  : 5,481,008
DATED       : January 7, 1996
INVENTOR(S) : Emil A. Broger, et al.

It is certified that error appears in the above-indentified patent and that said Letters Patent is hereby corrected as shown below:

Claim 5, column 14, line 11, "are S the same" should read --are the same--.

Signed and Sealed this

Twenty-sixth Day of March, 1996

Attest:

BRUCE LEHMAN

*Attesting Officer*      *Commissioner of Patents and Trademarks*